United States Patent [19]
Edwards

[11] Patent Number: 5,256,966
[45] Date of Patent: Oct. 26, 1993

[54] METHOD FOR DETECTING FLAWS IN A STEAM GENERATOR TUBE USING A FLEXIBLE EDDY CURRENT PROBE HAVING COIL BANK SWITCHING

[75] Inventor: Lawrence J. Edwards, Suffield, Conn.

[73] Assignee: Combustion Engineering, Inc., Windsor, Conn.

[21] Appl. No.: 687,750

[22] Filed: Apr. 19, 1991

[51] Int. Cl.⁵ .............................................. G01N 27/82
[52] U.S. Cl. ..................................... 324/220; 324/232; 324/238
[58] Field of Search .......................... 324/219–221, 324/225–227, 236–238, 239–243, 262

[56] References Cited

U.S. PATENT DOCUMENTS

| | | | |
|---|---|---|---|
| 3,284,702 | 11/1966 | Aunby et al. | 324/220 |
| 3,609,531 | 9/1971 | Förster | 324/227 |
| 3,681,682 | 8/1972 | Cox et al. | 324/227 X |
| 3,735,247 | 5/1973 | Harker | 324/227 X |
| 4,439,730 | 3/1984 | Kauffman | 324/232 |
| 4,468,619 | 8/1984 | Reeves | 324/220 |
| 4,742,298 | 5/1988 | Ando et al. | 324/220 |
| 4,808,924 | 2/1989 | Cecco et al. | 324/220 |
| 4,808,927 | 2/1989 | Cecco et al. | 324/220 |
| 4,851,781 | 7/1989 | Marzetta et al. | 324/366 X |
| 4,856,337 | 8/1989 | Metala et al. | 73/601 |
| 4,875,007 | 10/1989 | Ginns | 324/227 X |
| 4,876,506 | 10/1989 | Brown et al. | 324/220 |
| 5,047,719 | 9/1991 | Johnson et al. | 324/262 X |

FOREIGN PATENT DOCUMENTS

| | | | |
|---|---|---|---|
| 650012 | 10/1962 | Canada. | |
| 61-198055 | 9/1986 | Japan | 324/220 |
| 1462173 | 2/1989 | U.S.S.R. | 324/220 |

OTHER PUBLICATIONS

"Insertion Eddy Current Flaw Detecting Probe of the Switching Type", Mitsubishi Heavy Industries, Ltd., Jul. 12, 1982.

Primary Examiner—Gerard R. Strecker
Assistant Examiner—Warren S. Edmonds
Attorney, Agent, or Firm—Ronald P. Kananen; John H. Mulholland

[57] ABSTRACT

A method and apparatus for inspecting the profile of the inner wall of a conduit, such as a heat exchanger in a steam generator by a probe body that includes eddy current sensing coils. The number of eddy current sensing coils is increased for more completely sensing the conduit surface without a corresponding increase in coaxial cables by the use of a bank switch which switches respective banks of coils to existing conduits.

2 Claims, 4 Drawing Sheets

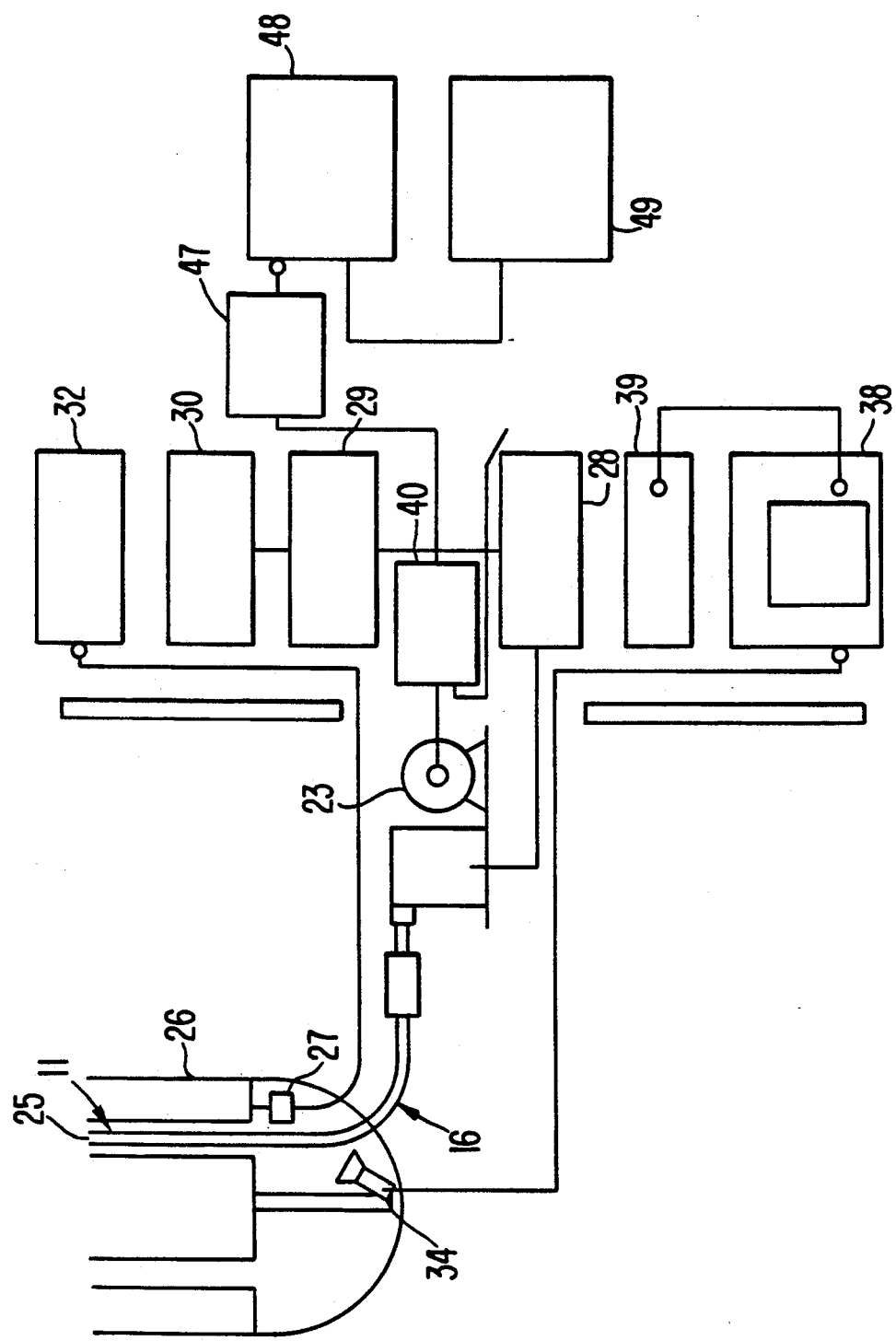

METHOD FOR DETECTING FLAWS IN A STEAM GENERATOR TUBE USING A FLEXIBLE EDDY CURRENT PROBE HAVING COIL BANK SWITCHING

BACKGROUND OF THE INVENTION

This invention relates to a method and apparatus for inspecting the profile of the inner wall of a conduit, such as a heat exchanger tube in a steam generator, by a probe body that includes eddy current sensing coils. More particularly, this invention relates to a method and apparatus wherein the number of eddy current sensing coils used for sensing the conduit is increased without a corresponding increase in coaxial cables by the use of a bank switch. Still more particularly, this invention relates to a combination of a solid state switching circuit located in an eddy current sensing probe which houses eddy current coils for switching between respective sets of coils to increase the number of coil sensors without correspondingly increasing the number of coaxial cables.

The in-service inspection of heat exchanger and steam generator tubing in nuclear power plants, as well as in other energy sources, often requires that special eddy current probes be used to detect flaws such as circumferential cracks in the tube wall which are not detected by the standard bobbin eddy current probe. Thus, probes for inspecting the inner walls of metallic conduits are known to the art. One type of such probe is an eddy current probe having eddy current coils located on a probe body which is inserted into the interior of a tube and translated rotationally along its longitudinal axis. The probe body accommodates differences in the radius of the internal tube walls by using spring fingers which flex in a radial direction. Such eddy current type probes are generally formed by an eddy current coil resiliently mounted in a probe head which engages the interior of the tube being inspected when the probe is rotated. The probe coil is electrically connected to a current generator which conducts an alternating current to the coil as it is moved. An impedance detecting circuit which may take the form of an inductive bridge is also connected across the leads of the coil.

In operation, the alternating current conducted through the coil excites it into generating a pulsating magnetic field whose magnitude and polarity changes in accordance with the frequency of the current. When the coil of the probe is positioned in the vicinity of an electrically conductive wall, the changing magnetic flux emanating from the coil induces eddy currents in a portion of the wall. The characteristics of the eddy currents produced are dependent in part upon the specific impedance of the portion of the wall that conducts the eddy current. Since flaws in the metal walls create regions of higher resistance at flaw locations, eddy current probes may thus be used to locate flaws by constantly monitoring the impedances of the sensing coils as the probe body is moved along a predetermined path along the internal walls of the tube.

Representative examples of such apparatuses including means for moving the probe within the tube are shown in U.S. Pat. No. 4,876,506 to Brown et al, and U.S. Pat. No. 4,856,337 to Metala et al.

One such probe proposed in the prior art uses an eight-coil array to provide the required sensitivity for detecting tube flaws in a steam generator. However, the system lacks an ability to examine 100% of the circumference of the steam generator tube because of the positioning requirements of the coil and the corresponding conduit arrangements. Thus, the spaces between the coils effectively provide undetected spaces and may allow a flaw to remain undetected and thus become a safety as well as commercial concern for the plant owner.

Other methods are used to inspect 100% of the tube circumference, but in general such methods are more complicated. For example, these methods include rotating eddy current and rotating ultrasonic probes. Both of these methods have disadvantages for requiring considerably more time than the eight coil array probe for acquisition and analysis of the data.

Accordingly, it is an overall problem in the art to increase the coverage of an eddy current array probe. While this problem might be solved in a number of ways including redesign of the coil, or increasing the number of coils, the latter approach generally requires that the number of coaxial cables in the probe also be increased. The coaxial cables in the existing probes presently constitute a bulky arrangement which limits equipment usage used to deliver the probe through the tubing.

In current arrangements, as is well known, the probe assembly which connects the probe head housing the coils to the eddy current tester must be wound on a reel of a probe pusher to be driven through a curved conduit and along the bends in the steam generator tube. Additional coaxial cables to accommodate more coils would not allow sufficient flexibility to permit the probe manage normal bends in this steam generator.

A prior proposal to be applied to an ordinary insertion type probe employed in eddy current flaw detecting of various heat transfer tubes suggested the use of a number of small size coils arranged about the circumference of the probe and utilized a time sharing arrangement from the coils with a switching and signal processing circuit to convert the information into parallel signals using two coils per segment and four sets of coils. That system contemplated the same number of cables as the number of coil segments, recognizing that an increase in the number of cables between the probe and the flaw detector reduces the cable flexibility. Accordingly, the switching element for multiplexing was mounted on the probe for converting the change in the impedance occurring in the sets of coils in the probe into the time sharing signals switched every half cycle of a clock set at, for example, 6 KHz. Such a circuit required complexities in the circuitry to perform the multiplexing operation.

Accordingly, it is an overall object of this invention to provide an eddy current probe having an enhanced number of coils divided into two banks of coils while utilizing a conventional coil conduit system for the use of a switching circuit for switching the cable from one bank of coils to another.

It is another object of this invention to provide a semiconductor switching circuit in the probe head which houses the eddy current coils to switch between two sets of coils.

It is another object of this invention to increase the number of coils in a probe head which houses the eddy current coils from a normal set, such as eight, to an enhanced set, such as sixteen, without the addition of any additional coaxial cables connecting the coils to the head.

These and other objects of this invention will become apparent from the written description of the invention which follows, taken in conjunction with the accompanying drawings.

BRIEF SUMMARY OF THE INVENTION

Directed to achieving the foregoing objects and overcoming the problems in the prior art, in one aspect, the invention relates to a probe head for insertion into a tube to be inspected, wherein the head comprises a plurality of eddy current coils located about the circumference of said head to scan an interior wall of said tube upon insertion in the tube and rotation within the tube by a probe apparatus. The plurality of coils comprises at least two sets of coils, each set having at least one coil in the set, one of the sets of coils being the same in number as a plurality of coaxial cables connecting said coils to instrumentation for measuring impedance changes in said coils indicative of flaw detection. A switch is located on the probe for switching between the sets of coils to respectively connect these sets of coils to the instrumentation. In a preferred embodiment, eight coaxial cables are used to connect eight coils in the head, and an additional eight coils are provided in the head to be respectively switched to the instrumentation by the switch.

The coils may be provided adjacent one another about the circumference of the probe, or one set of coils may be provided in adjacent circumferential paths axially spaced along the axis of the probe to provide substantially complete coverage of the interior of the tube as the probe transverses the interior of the tube. Preferably, the switch is an MOS semiconductor switch which exhibits low resistance when switched to the ON position to minimize deleterious effects on the eddy current signal. Such switch is resistant to the effects of radiation when used in nuclear power plants. A method of using such a probe is also disclosed.

Such a method and apparatus improve coverage of the steam generator resulting in an increased probability that all flaws will be detected and the safety of the plant will be improved while reducing outages due to failed tubes. In addition, data acquisition occurs with the fastest possible speed resulting in a commercial acceptance without additional changes to the hardware or software required for or used in previous commercial embodiments, thus resulting in ready commercial acceptance.

These and other features of the invention will become apparent from a detailed description of the invention which follows, taken in conjunction with the accompanying drawings.

BRIEF DESCRIPTION OF THE DRAWINGS

FIG. 1 is a schematic non-detailed diagram of an eight coil array probe wherein

FIG. 2 shows a typical data acquisition system for the eddy current testing of steam generator tubes;

FIG. 3 shows a multi-element absolute mode eddy current probe according to the invention having an enhanced number of coils, wherein

DETAIL DESCRIPTION OF THE PREFERRED EMBODIMENT

Figure 1A:
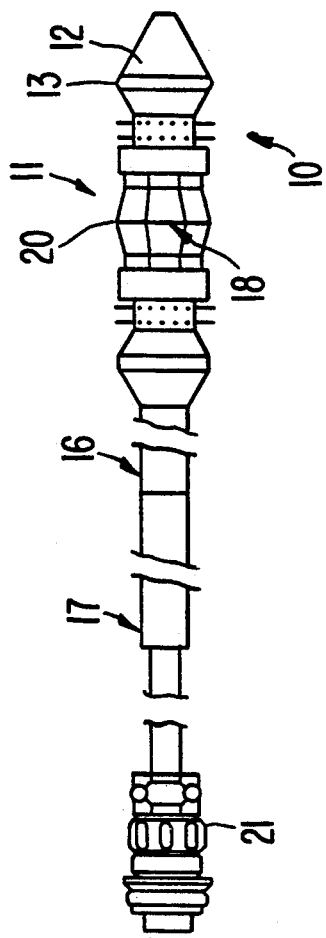
FIG. 1A shows the probe connected to a flexible shaft to a connector for a connection to upstream probe assembly instrumentation.

A conventional eight coil array probe assembly is designated generally by the reference numeral 10. The assembly includes a probe head 11 having a forward head piece 12 with a predetermined outside diameter (OD) 13 which, as can be seen in FIG. 1B is slightly less than the anticipated internal diameter (ID) of a tube 14 through which the probe assembly will pass. The probe head 11 is connected to a shaft 17 connected to a flexible member 16 which encloses a plurality of coaxial cables 19 which are the same in number as the coils 18 spacedly located on the head 11. Specifically, in the embodiment shown and known to the prior art, eight coils were used spaced circumferentially about the circumference of the probe head 11 along the circumferential line 20 in the spaced array, as will be discussed in greater detail. The shaft 17 is connected to a connector 21 for connection to suitable electronics as shown in FIG. 2. Such a probe is conventional and well known in the art, so further description of how to make and use such an assembly is not necessary.

In FIG. 2, an eddy current test equipment set up is shown in which the probe 11 is inserted into the tube 25 of a steam generator 26. As explained, the probe 11 is connected to a flexible member 16 under the control of an eddy current probe pusher 22 and take-up reel 23 which is commercially available. The eddy current probe pusher 22 and the take-up reel 23 are under the control of an operator at an operator position 28 respectively connected through an appropriate control network 29 and an operator positioner 30, the details of which will depend on a particular installation, but which are well known in the art. A positioner control member 32 controls the signal to the eddy current probe positioner 27. If desired, a TV camera 34 may be provided in the steam generator 26 to view the insertion of the probe 11 into the tube 26, the output of which is provided to a monitor 38 for recording by a VTR 39. The actual position of the probe 11 relative to the tube is coordinated by the circuit 40 whose coordinates axially and rotationally within a steam generator are connected via an interface 47 to a computer 48 for recording by a recording unit 49. Such units are well known in the art and conventional for receiving signals from the coils in the eddy current probe to provide position information and data for determining flaws.

Figure 1B:
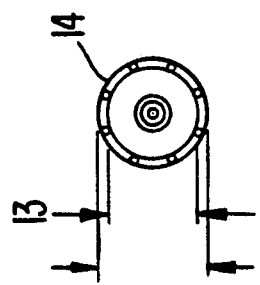
FIG. 1B shows an end view of the probe relative to the nominal tube ID.
Figure 3A:
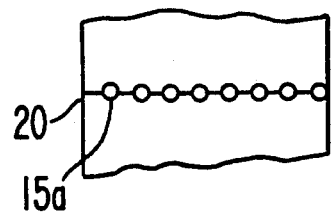
FIG. 3A shows a prior art eight coil probe spaced in an array in the probe.
Figure 4B:
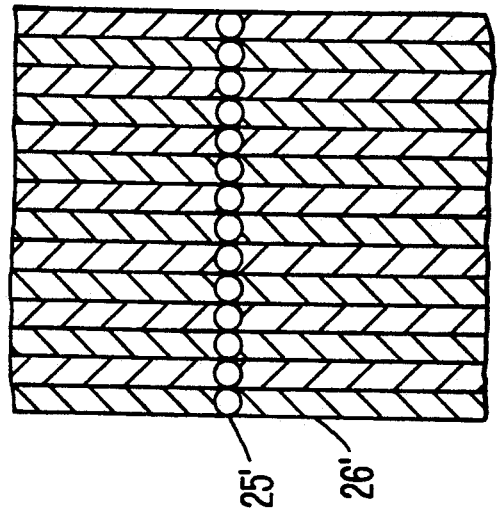
FIGS. 4A and 4B shows a scan by rotation of the probe of FIG. 3A in comparison to the more complete coverage provided by scan with the probe of FIG. 3B, when the interior of its tube scanned is projected.
Figure 4A:
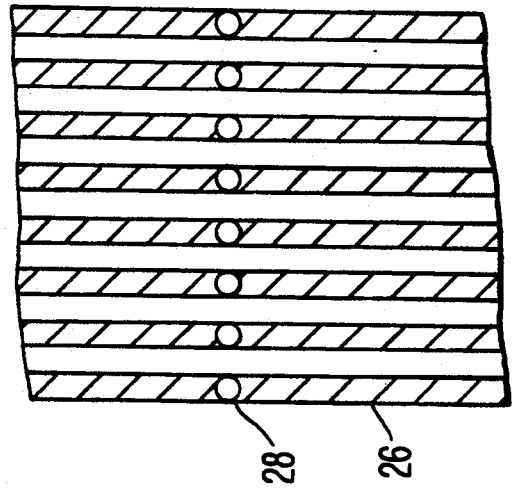

In FIG. 3A, the eight coil probe of the type shown in FIG. 1A is shown having coils 18, and specifically eight coils 15a to 15h substantially adjacently aligned, but spaced along the circumferential path 20. As shown in FIG. 4A, such a spaced arrangement provides a plurality of scan paths (when the probe is rotated); thus, the map of coverage shown in FIG. 4A of the projected interior of the tube is incomplete as indicated by the hatched paths 25 contrasted with the unhatched paths 26.

Figure 3B:
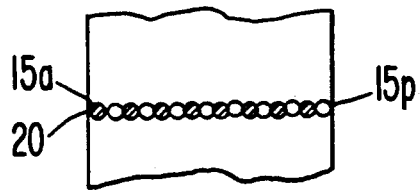
FIG. 3B shows a sixteen coil probe according to the invention with coils tightly spaced along a circumferential line of probes and FIG. 3C shows the general arrangement of two axially spaced coil sets in the probe head in circuit with a bank switch, the coaxial cables, and the eddy current tester frequency generator.

FIG. 3B shows an arrangement according to the invention in which sixteen coils 15a to 15p are provided on the circumferential path 20, one adjacent the other wherein the prior eight coils are shown as light circles, while the new coils are shown as dark circles. A map of the coverage provided by such an arrangement is that the coils are arranged to substantially completely cover the map of the projection of the interior of the coil, as seen by the respective areas, 25' and 26' in FIG. 4B. As is clear, data are available for the area 26.

Figure 3C:
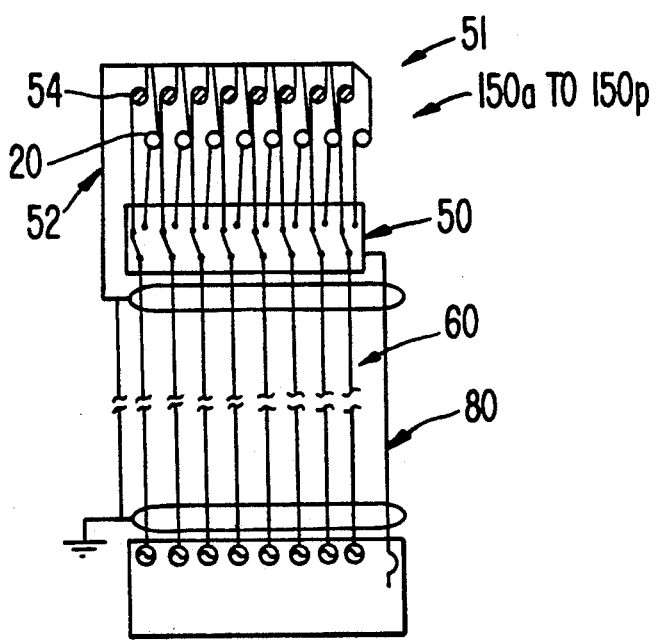

FIG. 3C, therefore, shows such a sixteen coil arrangement 15a to 15p in circuit with a solid state electronic bank switch 50 for switching between a first coil set 51 (coils 15a to 15h) and a second coil set 52 (coils 15i to 15p) located on the probe head 11. Preferably, the first coil set 51, the second coil set 52, and the bank switch 50 are located on the probe head of the probe assembly. The outlet side of the bank switch 50 is respectively connected to each of the coils in both coil sets 51, 52 while the inlet to the bank switch 50 is connected with the eight coaxial cables which are respectively connected to the frequency generator at the eddy current tester. In the embodiment of FIG. 3C, the first coil set 51 and the second coil set 52 are axially spaced a slight distance along lines 20 and 54 for convenience in handling the connections without affecting the map of the coverage of FIG. 4B. In operation, the bank switch 50 receives a signal on a lead 80 in a coil package 60 to switch this bank switch between the respective coil sets 51 and 52. Preferably, the bank switch 50 switches all eight coils at the same time at a switching speed depending upon the data that are sought. Such a circuit has an advantage over multiplexing in its simplicity and in view of the fact that the number of coaxial cables is not increased.

While the new coil set added has the same number of coils as in the old set, such numbers need not necessarily be identical. For example, there could be eight coils in the original probe which according to the invention could be made as twelve coils using only six coaxial cables switching between respective sets of six probes. Alternatively, the switching could be between a set of eight coils and a set of four coils, or such other numbers are may be convenient. These and other objects of the invention will become apparent to one of ordinary skill in the art.

Figure 5:
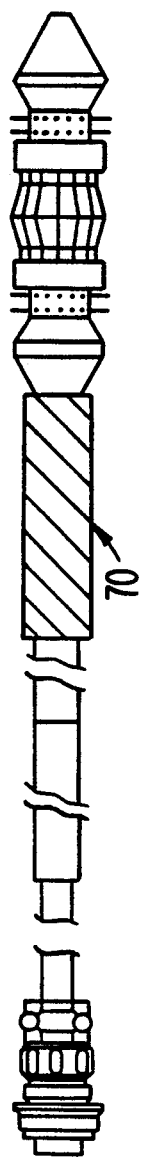
FIG. 5 is a view similar to FIG. 1 showing the probe of the invention.

FIG. 5 is substantially identical to FIG. 1, except that the probe portion having the reference numeral 70 includes the bank switch 50.

I claim:

1. A method of detecting flaws in a tube, comprising the steps of providing a probe assembly having a probe head with a plurality of coils, dividing said plurality of coils into a first set and a second set of coils, spacing said first set and said second set about a circumference thereof, switching between said first set and said second set of coils with a bank switch, and receiving at remotely located instrumentation output signals, which are transmitted over conductors from said coils, representative of said flaws.

2. The method as set forth in claim 1, further comprising the step of switching said bank switch to said other set of coils for connecting said other set to said plurality of cables.

* * * * *